(12) United States Patent
Yoshida et al.

(10) Patent No.: US 7,407,783 B2
(45) Date of Patent: Aug. 5, 2008

(54) FRUCTOSYLAMINE OXIDASE

(76) Inventors: Nobuyuki Yoshida, 102, Gakeunminamihaitsu, 15-35, Gakuenminami 3-chome, Nara-shi, Nara-ken (JP); Yoshiki Tani, 60-1, 56, Kamigamoshobuen-cho, Kita-ku, Kyoto-shi, Kyoto-fu (JP); Satoshi Yonehara, c/o ARKRAY, Inc., 57, Nishiaketa-cho, Higashikujo, Minami-ku, Kyoto-shi, Kyoto-fu (JP)

( * ) Notice: Subject to any disclaimer, the term of this patent is extended or adjusted under 35 U.S.C. 154(b) by 20 days.

(21) Appl. No.: 10/528,992

(22) PCT Filed: Sep. 16, 2003

(86) PCT No.: PCT/JP03/11766
§ 371 (c)(1),
(2), (4) Date: Jan. 10, 2006

(87) PCT Pub. No.: WO2004/029251
PCT Pub. Date: Apr. 8, 2004

(65) Prior Publication Data
US 2006/0172367 A1    Aug. 3, 2006

(30) Foreign Application Priority Data
Sep. 24, 2002 (JP) .............................. 2002-277214
Oct. 24, 2002 (JP) .............................. 2002-309734

(51) Int. Cl.
C12N 9/06       (2006.01)
C12N 9/00       (2006.01)
C12N 1/20       (2006.01)
C12N 15/00      (2006.01)
C12Q 1/00       (2006.01)
C12Q 1/42       (2006.01)
C07K 1/00       (2006.01)
C07H 21/04      (2006.01)

(52) U.S. Cl. .............................. 435/191; 435/4; 435/21; 435/183; 435/252.3; 435/320.1; 530/350; 536/23.2

(58) Field of Classification Search .................. 435/4, 435/21, 183, 191, 252.3, 320.1; 530/350; 536/23.1, 23.2
See application file for complete search history.

(56) References Cited

U.S. PATENT DOCUMENTS 5,712,138 A      1/1998  Kato et al.
2005/0101771 A1  5/2005  Kouzuma et al.

FOREIGN PATENT DOCUMENTS

EP    1 362 925 A1    11/2003
JP    10-201473 A      8/1998
JP    2002-218982 A    8/2002
WO    WO-02/061119 A1  8/2002

OTHER PUBLICATIONS

Accession AAW69251. Asahi Kasei Kogyo KK, Oct. 28, 1998.*
Database Genesequ Online. May 13, 2003, "Nucleotide sequence of fructosyl amino acid oxidase." Database accession No. ABV72307.
Database JPO Proteins Online. Feb. 18, 2003, "Fructosyl amino acid oxidase gene." Database accession No. BD579481.
Yoshida, N. et al., Appl. Environ. Microbiol., 1995, vol. 61, No. 12, pp. 4487 to 4489.
Regakado, V. et al., Applied Microbiology and Biotechmology, 1999, vol. 51, No. 3, pp. 388 to 390.

* cited by examiner

*Primary Examiner*—Tekchand Saidha
*Assistant Examiner*—Christian L Fronda
(74) *Attorney, Agent, or Firm*—Birch, Stewart, Kolasch & Birch LLP

(57) ABSTRACT

The present invention provides a fructosylamine oxidase which is obtainable by culturing *Fusarium proliferatum*, and purifying two types of fructosylamine oxidase (FAO) with different substrate specificities from the culture, and which is useful in the measurement of amadori compounds.

2 Claims, 6 Drawing Sheets

FRUCTOSYLAMINE OXIDASE

TECHNICAL FIELD

The present invention relates to a novel fructosylamine oxidase, more particularly, to a fructosylamine oxidase derived from *Fusarium proliferatum*, a process for preparing the same, and use thereof in the measurement of amadori compounds.

BACKGROUND ART

Amadori compounds are formed when a reactive substance having an amino group(s) such as protein, peptide or amino acid co-exists with a reducing sugar such as glucose in blood and food product. Thus, they combine together non-enzymatically and irreversibly through the amino group and aldehyde group, which is followed by amadori rearrangement to form an amadori compound. Since the production rate of an amadori compound is a function of concentration of reactive substances, contacting period, temperature, and the like, various information about a sample containing such reactive substances can be obtained from the amount of amadori compound. Therefore, analysis of amadori compounds is useful in the fields related to medicine, food, and the like. In the medical field, attention is particularly focused on the glycated protein as an index for diagnosis and control of conditions of diabetes. Diabetes causes various systemic symptoms (complications) such as diabetic retinopathy, diabetic nephropathy, diabetic neuropathy, and the like, and is the leading cause of blindness and introduction of dialysis. These complications are linked not only to the restriction of daily life and social activity of patients but also to the swelling medical expenses and raise a serious social problem. The importance of early detection and the following adequate control of blood glucose level has been indicated. As an index for controlling blood glucose in diabetes, glycohemoglobin reflecting the mean glucose level for the past about 1 to 2 months, glycoalbumin reflecting the mean glucose level for the past about 2 weeks, or fructosamine corresponding to glycated protein having reducing ability in serum is measured. Glycohemoglobin (HbA1c) is a glycated hemoglobin wherein α-amino group of valine at N-terminus of hemoglobin β chain is glycated. The measurement of HbA1c plays an important role in control of blood glucose level of diabetic patients.

The determination of amadori compound in enzymatic assay is carried out by contacting an amadori compound with an oxidoreductase, and measuring the amount of hydrogen peroxide produced or that of oxygen consumed. Fructosylamino acid oxidase, one of oxidoreductases, has generally been purified from microorganisms. See, for example, JP-H06-65300B, JP-H03-155780A, JP-H07-289253A ([00319, [0037]), JP-H08-154672A (Claim 2 and [0027]), JP-H11-243950A ([0037]) and JP-H05-192193A.

Enzymes described in these publications are explained in brief below. Enzymes from *Corynebacterium* include those specific for an amino acid glycated at α-amino group but not active on fructosyl lysine (hereinafter, it may be referred to as "FL"), which are poorly heat stable (90% or more activity is decreased by treatment at 45° C. for 10 minutes) and hence lack in sufficient practical usefulness (JP-H06-65300B). Enzymes from *Aspergillus* include those less active on FL compared to fructosyl valine (hereinafter, it may be referred to as "FV"); however, it is unknown whether or not the enzyme is active on glycated protein or hydrolysates thereof (JP-H03-155780A). Enzymes from *Gibberella* include those showing high specificity to fructosyl N α-Z-lysine (hereinafter, it may be referred to as "FZL"), of which α-amino group is protected, and being active on fructosylpolylysine but not active on fructosyl valine (JP-H07-289253A, [0031] and [0037]). Enzymes from *Fusarium* include those having the same or higher activity for fructosyl lysine compared to fructosyl valine (JP-H08-154672A, Claim 2 and [0027]). Other enzymes from *Fusarium* or *Gibberella* include those inactive on fructosyl valine but specific for fructosyl lysine (JP-H11-243950A, [0037]).

However, these existing enzymes are not satisfactory in terms of, for example, activity in the determination of glycohemoglobin, and therefore there has been a demand for an enzyme with high activity and excellent specificity. For instance, although these existing enzymes are active on glycated amino acids or poly-lysines produced by fragmentation with protease treatment or the like, they are almost inactive on glycated peptides in which the α-position is glycated. Accordingly, in the case of glycohemoglobin, wherein α-amino group of N-terminal amino acid is glycated, it is necessarily to release the N-terminal fructosyl valine certainly beforehand.

To measure glycated proteins accurately using an existing fructosylamino acid oxidase, it is generally inevitable to surely release the glycated amino acid as a substrate of the enzyme. However, there have not been provided any methods by which the glycated amino acid of interest can be surely released or proteases which are highly specific enough to make it sure the same. One of strategies to solve this issue is to use a fructosylamine oxidase reactive on peptide itself which is glycated at N-terminus. It is particularly important to use a fructosylamine oxidase that is also active on glycated peptides as fragmentation products so that one can measure accurately the hemoglobin A1c (HbA1c) which is significant in control of diabetes.

DISCLOSURE OF INVENTION

The present invention provides a novel fructosylamine oxidase (hereinafter, it may be referred to as "FAO") useful in the accurate and efficient measurement of amadori compounds, specifically, glycated proteins.

The present inventors have intensively studied and found that a strain of *Fusarium* produces FAO with excellent substrate specificity and established the present invention.

Thus, the present invention provides s fructosylamine oxidase derived from *Fusarium proliferatum*.

BEST MODE FOR CARRYING OUT THE INVENTION

Figure 1:
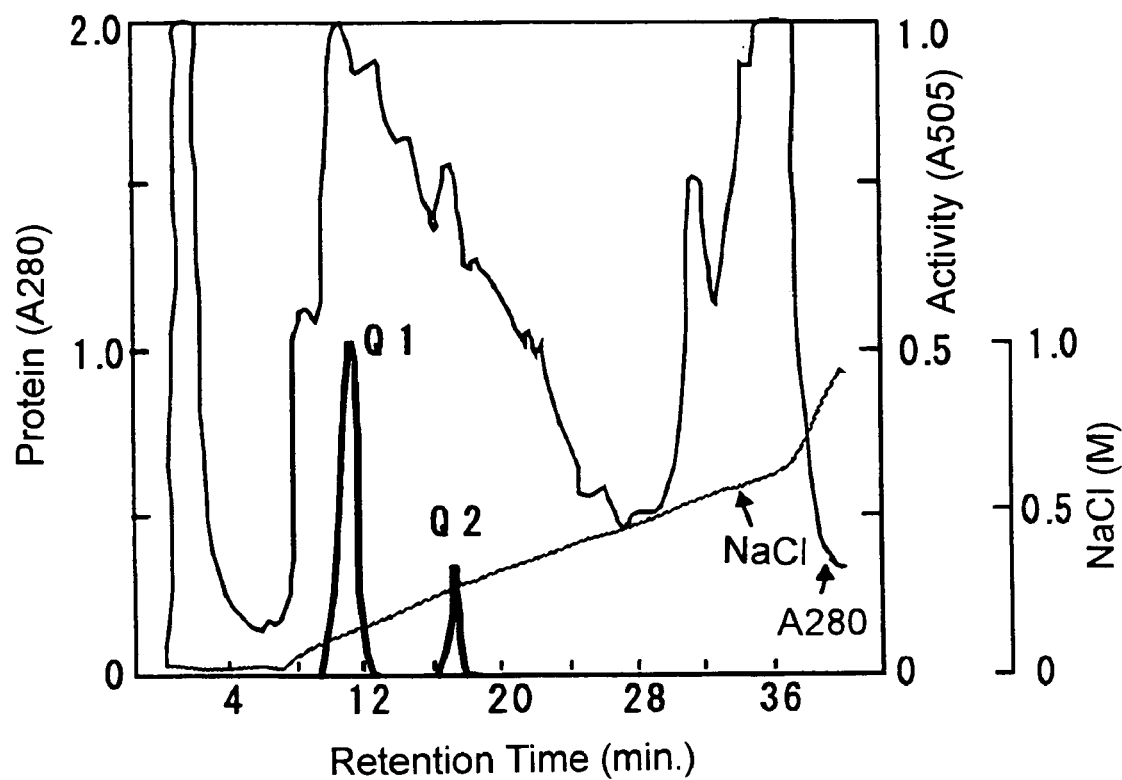
FIG. 1 shows the elution pattern from Resource Q column chromatography of protein (OD=280 nm) and activity of cultured *Fusarium proliferatum*.

The fructosylamine oxidase of the present invention has a catalytic activity in a reaction shown by the scheme (I).

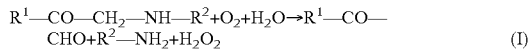

$$R^1-CO-CH_2-NH-R^2+O_2+H_2O \rightarrow R^1-CO-CHO+R^2-NH_2+H_2O_2 \quad (I)$$

wherein $R^1$ is $-[CH(OH)]_n-CH_2OH$ (wherein, n is 5 or 6), and $R^2$ is an amino acid residue or a peptide residue consisting of 2 to 10 amino acids.

In the scheme (I) above, $R^2$ is an amino acid residue or a peptide residue consisting of 2 to 10 amino acids, preferably an amino acid residue or a peptide residue consisting of 2 to 6 amino acids, and more preferably an amino acid residue or a peptide residue consisting of 2 to 3 amino acids.

Amino acid(s) constituting $R^2$ varies depending on the amadori compound to be determined; however examples include valine, lysine, histidine, leucine, serine and the like. When $R^2$ is a peptide residue, it may consist of 2 to 10 amino acids with valine or leucine at the N-terminus. More preferred peptide may consist of 2 or 3 amino acids with valine at the N-terminus, and examples include valine-histidine and valine-histidine-leucine.

When the FAO of the present invention is used in the measurement of HbA1c, it is preferred that said FAO is active on valine glycated at α-amino group, i.e., fructosyl valine (FV) or a peptide having FV at the N terminus, as described above. On the other hand, when the FAO is used in the measurement of glycated albumin wherein ε-amino group of lysine is glycated, it is preferred that said FAO is active on lysine glycated at ε-amino group, such as fructosyl lysine (εFL) or a peptide comprising εFL.

The FAO of the present invention is not limited to the one derived from a particular origin as far as it has an enzyme activity. For example, an FAO which is produced by a microorganism growing in a medium containing a given glycated amino acid or glycated peptide as the sole carbon and nitrogen sources and showing enzyme activity on glycated amino acid and glycated peptide as a substrate is useful for the present invention. Examples of glycated peptide used in the screening of such a microorganism include a product of fragmentation of an objective glycated protein. An objective FAO can be obtained by culturing microorganisms in a medium containing such a glycated peptide as the sole carbon and nitrogen sources, purifying the resulting enzyme and confirming the activity. As will be described hereinafter, the inventors have screened microorganisms in soil using fructosyl valine-histidine-leucine (FVHL) and found out a microorganism of *Fusarium* having an FVHL assimilating ability.

Since the FVHL above is the same as the N-terminal sequence of hemoglobin β-chain, it is suitable for screening of FAO useful in the measurement of HbA1c. Such a glycated peptide can be prepared according to a method known in the art.

Thus, the FAO of the present invention can be prepared microbiologically using a *Fusarium* strain. Preferred microorganisms include *Fusarium proliferatum* or variants thereof.

*Fusarium proliferatum* is a strain which the present inventors have isolated from soil for the first time according to the method described in Example 1. It had been deposited with the "International Patent Organism Depositary, National Institute of Bioscience and Human-Technology", Central 6, 1-1-1 Higashi, Tsu-kuba-shi, Ibaraki-ken, Japan (*Fusarium* sp. GL2-1 strain; received date: Sep. 9, 2002; accession number: FERM P-19005), and has been transferred to international deposit (transfer date: Aug. 11, 2003; accession number: FERM BP-8451). Hereinafter, *Fusarium proliferatum* of the present invention may be referred to as "GL2-1" or "GL2-1 strain".

It is possible to derive strains having an improved activity on FVHL or other substrates from GL2-1, the original strain, by means of mutagenesis or gene recombination techniques. Such a variant can also serve as the source of FAO of the present invention. The derivative strains include those obtained artificially by mutagenesis or those obtained by screening.

The FAO of the present invention can be prepared by culturing a microorganism capable of producing FAO in a glucose-valine browning medium (hereinafter, referred to as "GV browning medium"). The GV browning medium can be obtained by autoclaving glucose and valine at 120° C. for 30 minutes. Examples of preferred GV browning medium includes a medium containing 1.5% glucose, 0.5% L-valine, 0.1% $K_2HPO_4$, 0.1% $NaH_2PO_4$, 0.05% $MgSO_4.7H_2O$, 0.01% $CaCl_2.2H_2O$ and 0.2% yeast extract.

Typically, cultivation is performed at 25-37° C., preferably at 28° C. The pH of medium is between 4.0 and 8.0, preferably between 5.5 and 6.0. However, the conditions are not critical and should be adjusted appropriately depending on the conditions of respective microorganisms and are not limited to the conditions described above.

When GL-2 strain is cultured under the above conditions for 12-36 hours, preferably for 24 hours, an FAO is accumulated in fungal cells. A cell-free extract can be obtained in a conventional manner by collecting fungal cells by filtration followed by centrifugation. The grinding of cells can be carried out in a conventional manner, for example, by means of mechanical grinding, autodigestion using a solvent, freezing, ultrasonic treatment, pressurization, or the like.

The method of isolation and purification of an enzyme is also known in the art. It can be conducted by combining appropriately known methods including salting-out with ammonium sulfate, precipitation with an organic solvent such as ethanol, ion-exchange chromatography, gel filtration, affinity chromatography, and the like.

For example, mycelia can be harvested from resultant culture by centrifugation or suction filtration, washed, suspended in 0.1 M Tris-HCl buffer (pH 8.0) containing 1 mM DTT, ground (broken) with Mini-BeadBeater™ (0.5 mm glass beads), and centrifuged. The supernatant as a cell-free extract is then purified by ammonium sulfate fractionation, dialysis and column chromatography using Resource Q column (Amersham Biosciences).

Alternatively, when an FAO is secreted or accumulated in medium, the enzyme can be separated and purified according to a method known per se, for example, by an appropriate combination of methods including ion-exchange resin treatment, activated carbon absorption treatment, precipitation from organic solvent, vacuum concentration, freeze-drying, crystallization, and the like.

According to the method above, at least two FAOs have been obtained from GL2-1 strain, which FAOs show different retention times on Resource Q column chromatography. One of the FAOs is active on both of fructosyl valine (FV) and N-α fructosyl lysine (FZL) (hereinafter, referred to as "FAO-Q1"), and the other is active on FV but inactive on FZL (hereinafter, referred to as "FAO-Q2"). Although the preparation and identification is herein described in relation to FAO-Q1 and FAO-Q2 derived from GL2-1 strain, the present invention is not limited to an enzyme of particular origin and includes any FAOs which are useful for the purpose of the present invention and have the physicochemical characteristics shown below.

The enzymes of the present invention derived from GL2-1 strain will be hereinafter described in more detail.

FAO-O 1

1) It is almost equally or more active on fructosyl valine as compared to fructosyl lysine;
2) The optimum pH for enzyme reaction is 7.5;
3) The optimum temperature for stability of enzyme is about 30-40° C.; and
4) The molecular weight is about 39 kDa when estimated by SDS-PAGE, and is about 39.4 kDa when estimated by gel filtration. FAO-O2

1) It is not detectably active on fructosyl lysine but is active on fructosyl valine;
2) The optimum pH for enzyme reaction is 7;
3) The optimum temperature for stability of enzyme is about 30-40° C.; and
4) The molecular weight is about 49 kDa when estimated by SDS-PAGE, and is about 58 kDa when estimated by gel filtration.

General characteristics of these two types of enzymes are described below.

1. Normal Induction Characteristics

They are inducible enzymes that could be induced by FVHL, and are induced in a medium containing FVHL as the sole carbon and nitrogen sources.

2. Reaction Specificity and Substrate Specificity

As described in Example 2(1), enzymes partially purified from GL2-1 strain culture gave active fractions Q1 and Q2 of different retention times on Resource Q column chromatography. Each fraction contained an enzyme herein referred to as "FAO-Q1" and "FAO-Q2", respectively. As mentioned above, FAO-Q1 was almost equally active on both of FV and FZL, and on FVL as well. On the other hand, FAO-Q2 was active on FV as well as FVH and FVHL, of which N-terminal valine is glycated, but was inactive on FZL.

3. pH and Temperature Conditions

Determination of Optimum pH

Enzyme reaction was conducted under different pH conditions between 3.5 and 10.0 according to the method for determination of activity as described above.

Figure 2:
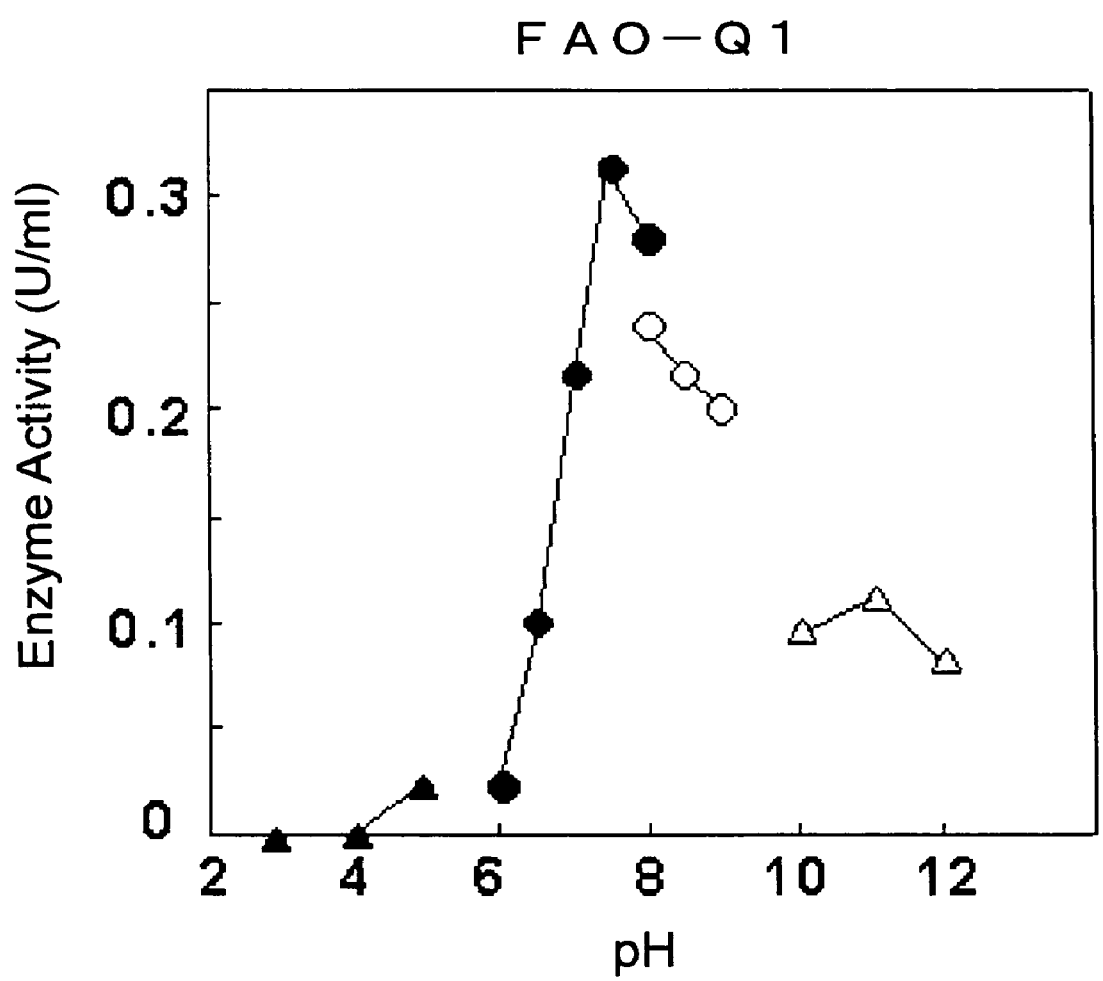
FIG. 2 is a graph showing the relationships between the activity of FAO-Q1 in a solvent and pH, which FAO-Q1 is one of enzymes of the present invention.
Figure 3:
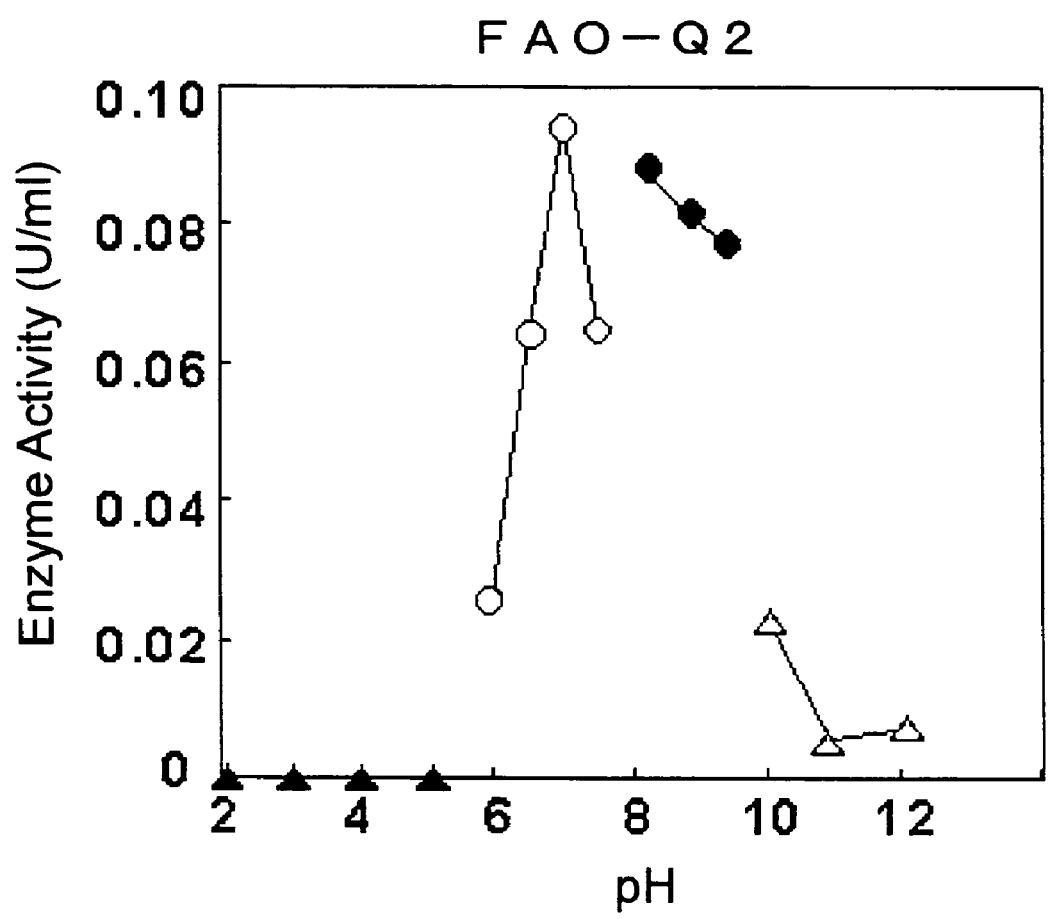
FIG. 3 is a graph showing the relationships between the activity of FAO-Q2 in solvent and pH, which FAO-Q2 is one of enzymes of the present invention.

The buffers used were 100 mM acetate buffer at pH range of 3.5-6.0, 100 mM potassium phosphate buffer at pH range of 6.0-8.0, 100 mM Tris-HCl buffer (pH range of 7.0-9.0) and 100 mM glycin-NaOH buffer at pH range of 9.0-10.0. As shown in FIGS. 2 and 3, it was revealed that the enzyme FAO-Q1 of the present invention has a pH optimum of about 7.5 at 30° C., and FAO-Q2 of the present invention a pH optimum of about 7.0 at 30° C.

Determination of Optimum Temperature for Stability of Enzyme

Figure 4:
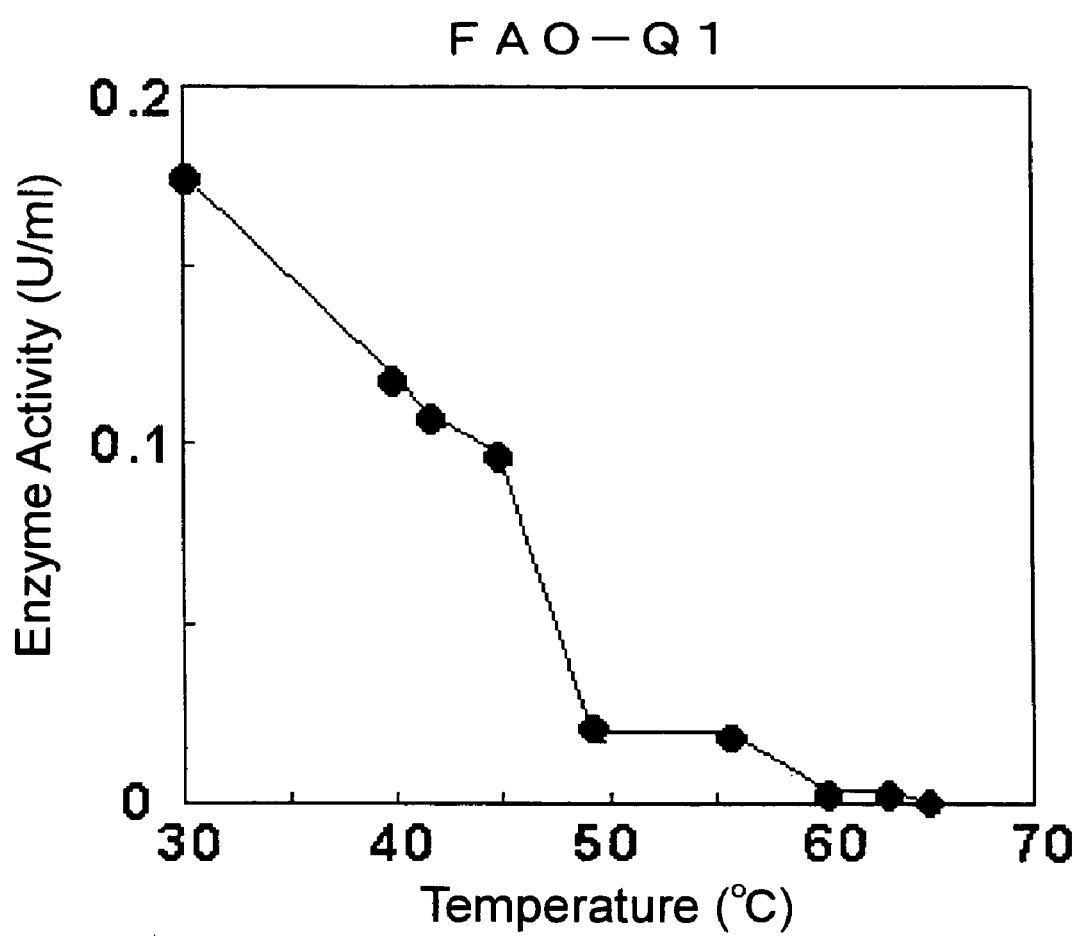
FIG. 4 is a graph showing the relationships between the activity of FAO-Q1 in a solvent and temperature.
Figure 5:
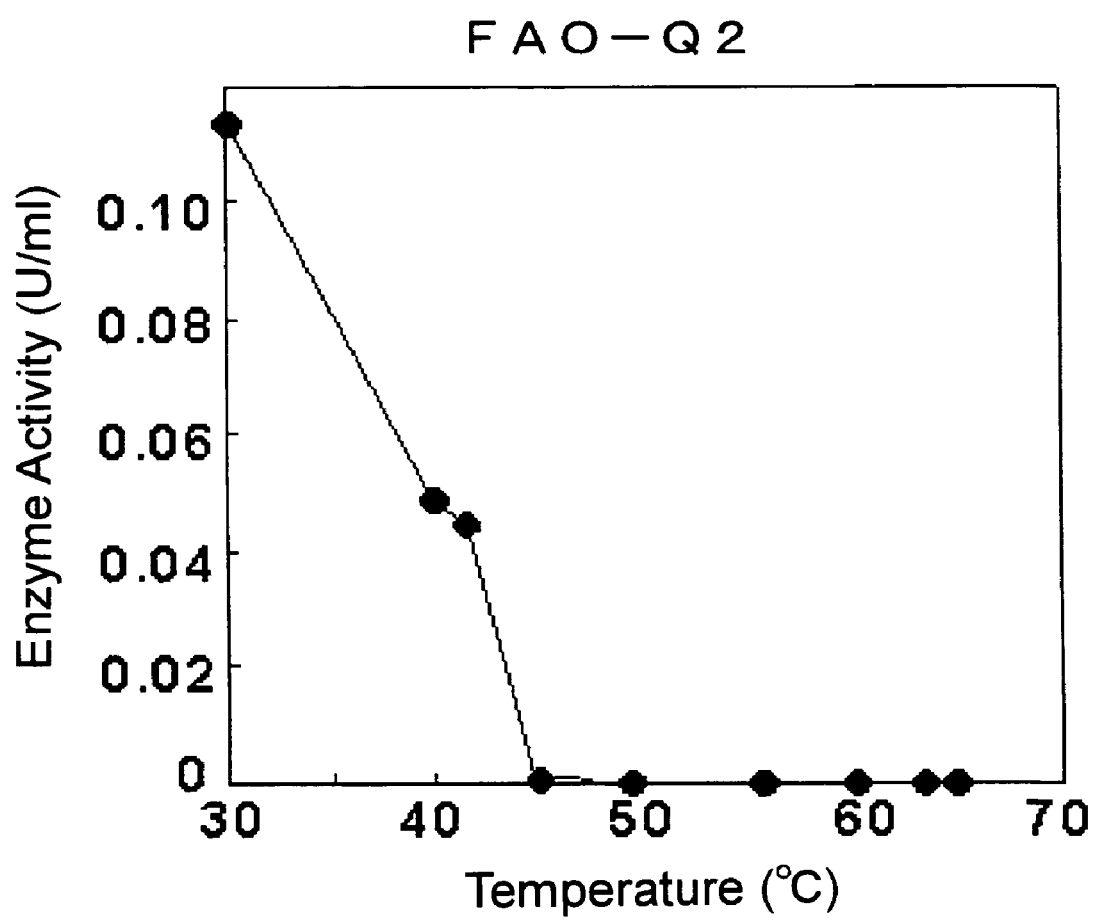
FIG. 5 is a graph showing the relationships between the activity of FAO-Q2 in a solvent and temperature.
Figure 6:
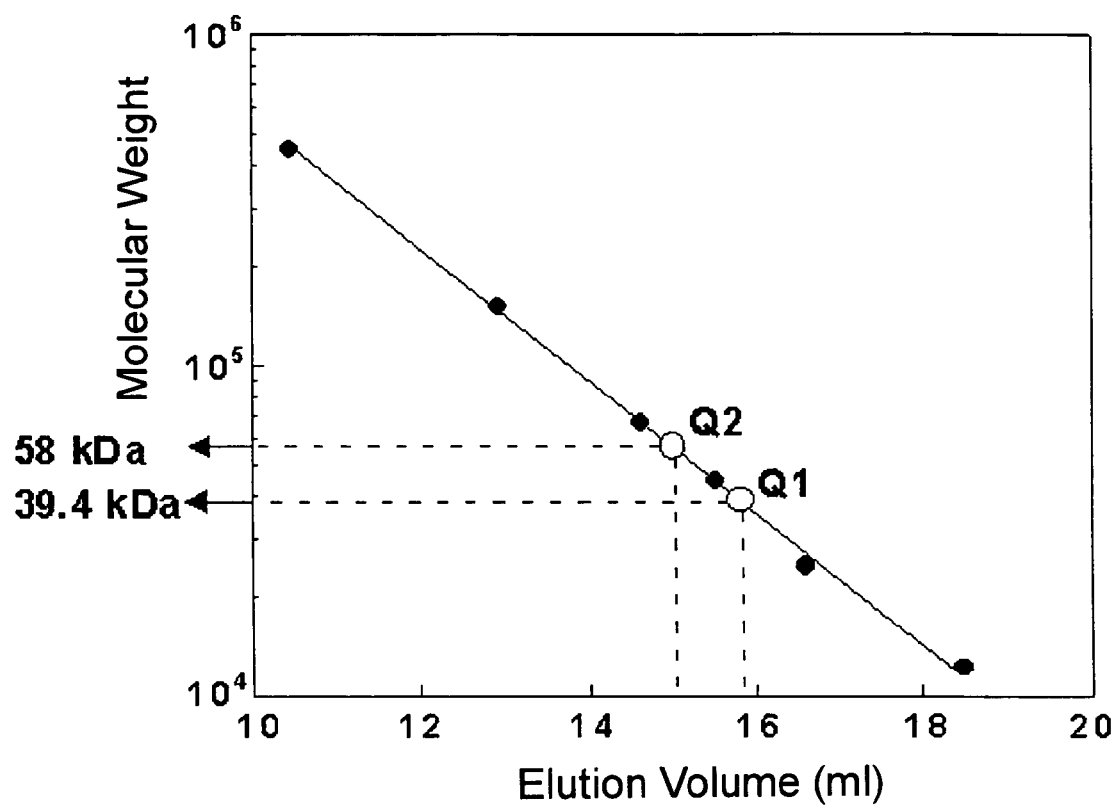
FIG. 6 is a graph showing the molecular weights of FAO-Q1 and FAO-Q2 determined by gel filtration.

Temperature conditions for the enzyme were determined by incubating FAO-Q1 or FAO-Q2 in 0.1 M Tris-HCl buffer (pH 8.0) at a temperature between 30 and 65° C. for 10 minutes, and measuring the activity under normal conditions. The results of measurement are shown in FIGS. 4 and 5. These figures show that the optimum temperature for enzymatic stability is between 30° C. and 40° C.

4. Evaluation of Titer

Titration of enzyme can be performed by a method known in the art (e.g., kinetic method), for example, that described in Example 1 (3). In this method, hydrogen peroxide generated by the reaction of an FAO with a glycated amino acid or peptide is measured on the basis of absorbance (505 nm) of quinone pigment produced in the presence of hydrogen peroxide. The amount (μmole) of hydrogen peroxide generated per minute is calculated on the basis of molar absorptivity ($5.16 \times 10^3$ $M^{-1}$ $cm^{-1}$) of quinone pigment and the resultant numerical value is taken as a unit (U) of enzyme activity.

The method of measuring activity is not limited to the above-described method, and the enzyme activity of the present FAO can be determined by other methods including an end point method, a method based on measurement of oxygen absorption, etc.

Determination of Michaelis Constant

Michaelis constant for respective substrates can be determined by measuring the initial reaction rate in the process for determination of titer as described above while keeping the conditions regarding enzyme concentration, pH, temperature, and the like constant and changing only the concentration of substrate.

Among FAOs of the present invention, FAO-Q1 shows almost the same activity on FV and FZL and therefore is widely useful for assay of amadori compounds. On the other hand, FAO-Q2 shows activity on FV but not on FZL, and therefore is useful for a selective assay of glycohemoglobin. Furthermore, FAO-Q2 is active on FVH and FVHL which are N-terminal sequence of glycohemoglobin. Accordingly, it becomes possible to determine only the glycosylation at N-terminus without measuring the internal glycosylation (ε-position) of glycohemoglobin molecule, whereby one can assay HbA1c more accurately.

When analyzing an amadori compound such as glycated protein using the present FAO, a sample containing an amadori compound(s) is contacted with an FAO of the present invention, and the amount of oxygen consumed or that of hydrogen peroxide generated is measured according to a known method. Any samples are available, and examples include those derived from a living body such as blood (e.g. whole blood, plasma or serum) and urine, and food products such as soy sauce, and the like. Blood-is an-especially preferred sample.

When an FAO of the present invention is used, the suitable reaction conditions such as pH and temperature are selected for respective enzymes. That is, when FAO-Q1 is used, the reaction could be carried out at pH range of about 6.5-12, preferably about 7-8, more preferably about 7.5; and at temperature range of 30-40° C.

When FAO-Q2 is used, the reaction could be carried out at pH range of about 6-10, preferably about 6.5-8, more preferably about 7; and at temperature range of 30-40° C. However, the conditions may be changed in accordance with the substrates or other reaction conditions etc., and are not limited thereto.

The amount of FAO used in an assay may be selected appropriately in accordance with the method used in the assay; however, it is generally 0.1 unit/ml or more, preferably 1-100 units/ml. As a buffer, Tris-HCl or the like can be used.

When analyzing a glycated protein using an FAO of the present invention, the protein is preferably subjected to fragmentation beforehand so that it releases an amino acid or peptide residue. Such methods including chemical and enzymic methods are known in the art. However, since the FAO of the present invention, especially FAO-Q2, is active on not only glycated amino acid but also glycated peptide as the degradation products of glycated protein, measurement can be carried out with good accuracy even if fragmentation treatment is not perfect.

Accordingly, the present invention also provides a method of measuring amadori compounds in a sample using the above-described FAO (FAO-Q1 or FAO-Q2).

An FAO used in the measuring method of present invention can be prepared by culturing Fusarium proliferatum (FERM BP-8451) producing FAO in a nutrient medium, and isolating and purifying resulting FAO of the present invention from the medium. The so obtained FAO, namely a naturally occurring FAO, may have naturally occurring modifications and mutations as far as it meets the purpose of the present invention. Furthermore, it may be accompanied by contaminants, other than the enzyme, resulting from the isolation and purification steps subject that they do not affect the accuracy and reliability of the measurement.

The FAO of the present invention can also be prepared according to the recombinant DNA techniques. Namely, recombinant proteins corresponding to FAO-Q1 or FAO-Q2 can be prepared in a conventional manner using a DNA encoding the amino acid sequence shown in SEQ ID NO: 4 or 6.

Thus, the present invention provides an FAO comprising the amino acid sequence shown in SEQ ID NO: 4 or 6.

As used herein, the term, "FAO (including FAO-Q1 and FAO Q2)" refers to, if not otherwise specified, both of an enzyme isolated from naturally occurring microorganisms and that obtained recombinantly.

The present invention also provides a DNA encoding FAO of the present invention.

The DNA of the present invention preferably encodes a protein comprising the amino acid sequence shown in SEQ ID NO: 4 or 6, and more preferably comprises the nucleotide sequence shown in SEQ ID NO: 3 or 5.

The process for preparing a recombinant protein by recombinant DNA technology is known in the art. For example, a recombinant protein having a desired activity can be prepared by introducing the DNA of the present invention into a suitable host, culturing the resultant transformant, and separating and purifying the FAO of the present invention from the culture. As is easily understood by one of ordinary skilled in the art, the recombinant FAOs of the present invention obtainable in this manner are not limited to those having the amino acid sequences shown in SEQ ID Nos. 4 and 6, and rather encompass proteins having an amino acid sequence derived from the said sequences according to a conventional manner and fragments of the amino acid sequences shown in SEQ ID Nos.4 and 6, as far as they fall within the definition above.

The preparation of recombinant FAO can be carried out according to a known method. For example, an expression vector for allowing expression of FAO in various hosts can be constructed by inserting a DNA encoding FAO into downstream from a promoter of suitable expression vector. The expression vector is then used to transform a suitable host cell. Examples of host cell include microorganisms [prokaryotes (bacteria, such as E. coli and Bacillus subtilis) and eukaryotes (such as yeast)], animal cells or cultured plant cells. An appropriate host-vector system for each host is known and expression using such a host cell can be performed by a method described in literatures (e.g., Molecular Cloning: A LABORATORY MANUAL, Cold Spring Harbor Laboratory Press), or by a known method.

Transformation of host cells with an expression vector can also be performed by a method described in literatures (e.g., Molecular Cloning, supra), or by a method known in the art.

The cultivation of resultant transformants can be carried out in a suitable medium selected from known media or a medium freshly prepared. The medium usually contains a carbon source (e.g., glucose, methanol, galactose, fructose, etc.) and an inorganic or organic nitrogen source (e.g., ammonium sulfate, ammonium chloride, sodium nitrate, peptone, casamino acid, etc.). Other nutrients such as inorganic salts (e.g., sodium chloride, potassium chloride), vitamins (e.g., vitamin B1), and antibiotics (e.g., ampicillin, tetracycline, kanamycin) can be optionally added to the medium. For mammal cells, Eagle's medium is preferred.

The cultivation of transformants is normally conducted at pH 6.0-8.0, preferably at pH 7.0, and at a temperature of 25-40° C., preferably at 30-37° C. for 8 to 48 hours. When the resulting FAO is present in the culture solution or filtrate thereof (supernatant), the cultured medium is filtered or centrifuged for separation. FAO can be purified from the filtrate/supernatant by a conventional method that is commonly used in the isolation and purification of a naturally occurring or a synthetic protein, which method includes dialysis, gel-filtration, affinity column chromatography using anti-FAO monoclonal antibody, column chromatography using an appropriate adsorbent, high performance liquid chromatography, and the like. When the resultant FAO is present in the periplasm or cytoplasm of cultured transformants, cells are harvested by filtration or centrifugation, and subjected to ultrasonic treatment and/or lysozyme treatment for destruction of cell walls and/or cell membranes to obtain cell debris. The debris is then dissolved in an appropriate aqueous solution such as Tris-HCl buffer. FAO can be purified from the solution in accordance with the aforementioned method. If a fragment(s) having enzyme activity is needed, it can be obtained by treating the FAO with an enzyme such as restriction enzyme or exonuclease. Thus, FAO can be prepared efficiently by means of recombinant technology using appropriate host cells.

The following Examples further illustrate the present invention in detail.

EXAMPLE 1

Screening and Identification of Microorganisms Producing FAO (1) Screening of Microorganisms Producing FAO Fructosyl valine-histidine-leucine (FVHL) which is the same as the N-terminal sequence of glycohemoglobin β chain was prepared by glycosylation of VHL. A method therefor is known to those skilled in the art.

FVHL-assimilating microorganism was isolated from soil using a medium (FVHL medium) containing FVHL as the sole carbon and nitrogen sources. Collected soil was added into 5 ml of FVHL medium in a test tube (16.5 mm in diameter), and cultured with shaking (300 rpm) at 30° C. for 48 hours.

| FVHL medium | |
|---|---|
| FVHL | 5 g |
| $K_2HPO_4$ | 1 g |
| $NaH_2PO_4$ | 1 g |
| $MgSO_4 \cdot 7H_2O$ | 0.5 g |
| $CaCl_2 \cdot 2H_2O$ | 0.1 g |
| Vitamin mixture * | 0.1% (v/v) |
| Metal solution ** | 1.0% (v/v) |
| Distilled water | q.s. |
| Total volume | 1,000 ml |

-continued

| *Vitamin mixture | |
|---|---|
| Thiamine HCl | 1 mg |
| Riboflavin | 2 |
| Calcium pantothenate | 2 |
| Pyridoxine HCl | 2 |
| Biotin | 0.1 |
| p-Aminobenzoic acid | 1 |
| Nicotinic acid | 2 |
| Folic acid | 0.1 |
| Distilled water | q.s. |
| Total volume | 100 ml |
| ** Metal solution | |
| $MnSO_4 \cdot 3H_2O$ | 1.7 g |
| $ZnSO_4 \cdot 7H_2O$ | 2.2 |
| $CuSO_4 \cdot 5H_2O$ | 0.4 |
| $CoCl_2 \cdot 2H_2O$ | 0.28 |
| $Na_2MoO_4 \cdot 2H_2O$ | 0.26 |
| $H_3BO_3$ | 0.4 |
| KI | 0.06 |
| Distilled water | q.s. |
| Total volume | 1,000 ml |

As a result, thirteen FVHL-assimilating strains were obtained, which were then subjected to cultivation and evaluation of activity as described below to select a microorganism strain(s) having FAO activity.

(2) Cultivation and Preparation of Cell-Free Extract

Each of 13 strains obtained in (1) above was cultured in glucose-valine (GV) browning medium and the crude extract solution was prepared therefrom.

| GV browning medium | |
|---|---|
| Glucose | 1.5% (w/v) |
| L-valine | 0.5 |
| $K_2HPO_4$ | 0.1 |
| $NaH_2PO_4$ | 0.1 |
| $MgSO_4 \cdot 7H_2O$ | 0.05 |
| $CaCl_2 \cdot 2H_2O$ | 0.01 |
| Yeast extract | 0.2 |

Cultivation was conducted by incubating in 5 ml of GV browning medium in a test tube (16.5 mm in diameter) with shaking (300 rpm) at 30° C. for 24 hours. A cell-free extract was prepared by filtering the culture solution through a filter, grinding the resultant mycelia with Mini-BeadBeater™ (0.5 mm glass beads), and centrifuging (4° C., 10,000×g, 10 minutes) the mixture, which was then used as a crude enzyme solution.

(3) Determination of FAO Activity

FAO activity of the crude enzyme solution was determined by the aforementioned rate method. The time-course of generation of hydrogen peroxide in the reaction mixture below was measured by a colorimetric method, and FAO activity was evaluated.

| Tris-HCl buffer (pH 8.0) | 100 μmol |
|---|---|
| 4-Aminoantipyrine | 4.5 μmol |
| Phenol | 6 μmol |
| FV | 5 μmol |
| Peroxidase | 6 units |
| Crude extract solution (cell-free extract) | 1 ml |
| Total amount | 3 ml |

A mixture (total 3 ml) except for the enzyme solution was equilibrated at 30° C. After adding the enzyme solution, the time-course of absorbance at 505 nm was measured. The amount (μmole) of hydrogen peroxide generated per minute was calculated on the basis of molar absorptivity ($5.16 \times 10^3$ $M^{-1}$ $cm^{-1}$) of quinone pigment produced, and the resultant numerical value was taken as a unit(U) of enzyme activity. As a result, a strain having FAO was obtained.

(4) Identification of Strain

Mycological Properties

The microorganism was seeded on a plate of potato dextrose agar (PDA), oatmeal agar (OA) or 2% malt agar medium (MEA), and cultured at 25° C. up to 8 weeks while observing the mycological properties. Description of color of colony is in conformity with the teaching of Komerup & Wanscher (1978).

Observation of Macroscopic Characteristics of Colony

The colony had a smooth edge and was slightly raised upward convexly.

Aerial hypha was fluffy and the color of the colony surface was white-reddish white (11A1-2) from the beginning. After 8 weeks, it was not observed any apparent changes in the degree of color development or the color of surface due to conidia insertion.

The color of colony on the backside was almost the same as that of the front side; slight pale red (11A3) color was observed in colonies cultured for a long time in PDA or MEA medium. Production of a small amount of clear exudate was observed in PDA or OA plate.

Observation of Microscopic Characteristics of Colony

Both the microconidium and macroconidium were observed.

Microconidium was of phialidic type and had a conidiophore structure like *Acremonium*. Conidiophore was almost straight and occasionally divided into two branches, and observed throughout the whole aerial mycelium. It was composed of one or two cells and sticky, and formed massive structure at the tip. The shape varied from ellipsoidal to fusiform shape and the surface varied from smooth to slightly rough surface.

Macroconidium was morphologically the same as that of *Fusarium*, composed of 3 to 6 cells, was in the luniform shape, and had a smooth surface and footcell. There were observed many short aerial mycelia with a thickness of from middle to slightly thin. The cell wall was weak and most of macroconidia were deficient in the surface.

Considering the results above, the microorganism was assigned to *Fusarium* on the basis of the classification scheme described in Arx (1974), Domish (1993) and Malloch (1981). There are genera having a similar morphology such as *Cylindrocarpon, Candelabrella, Monacrosporium, Trichophoron* and the like; however, the microorganism of the present invention differs from these genera in, for example, that the macroconidium is in luniform shape, the aerial mycelium does not form a ring and there exists microconidium, and meets the definition of *Fusarium* described in "Gene of Hyphomycetes" (Carmichael et al., 1980).

This strain has been deposited with the International Patent Organism Depositary, National Institute of Advanced Industrial Science and Technology under the accession number of FERM BP-8451 as "*Fusarium* sp. GL2-1 strain".

Identification of Species (Analysis of Ribosomal Base Sequence)

Identification of GL2-1 strain above was carried out by examining the sequence of 18S ribosome DNA (18SrDNA). The GL2-T1 strain was cultured in GV medium according to the method described in (2) above and DNA was prepared in a conventional manner from the resultant mycelia. The internal transcribed spacer sequence of rDNA was then amplified by PCR using the resultant DNA as a template, and the base sequence was analyzed (Mycopathologia Vol. 140 P35-49 1997). As a result, the base sequence shown in SEQ ID NO: 1 was determined. The homology search with said base sequence revealed that it was 100% homologous to *Fusarium proliferatum*.

EXAMPLE 2

Preparation of FAO Using GL2-1 and Identification of the Same (1) Partial Purification of FAO 1) Cultivation and Preparation of Cell-Free Extract A GL-2 strain identified in Example 1 was cultured in 100 ml of GV browning medium as described in Example 1 (2) under the same medium composition and culture condition.

After cultivation, mycelia were collected by filtering the culture medium through a filter. The resultant mycelia (0.6 g) were suspended in 0.1 M Tris-HCl buffer (pH 8.0) containing 1 mM DTT, ground with Mini-BeadBeater™ (glass beads 0.5 mm), and centrifuged (4° C., 10,000×g, 10 minutes) to obtain the supernatant as a cell-free extract.

2) Ammonium Sulfate Fractionation

Cell-free extract obtained in 1) was subjected to ammonium sulfate (30-80% saturation) fractionation by dissolving in 50 mM Tris-HCl buffer (pH 8.0) containing 1 mM DTT and dialyzing against the same buffer.

3) Resource Q Column Chromatography

The ammonium sulfate fraction after dialysis was subjected to chromatography under the following conditions.

| | Analysis condition |
|---|---|
| Column (volume): | Resource Q column (1 ml) (Amersham Biosciences K.K.) |
| Flow rate: | 1 ml/min |
| Buffer A: | 50 mM Tris-HCl buffer (pH 8.0) + 1 mM DTT |
| Buffer B: | Buffer A + 1 M NaCl |
| | Elution condition |
| 0-5 min: | 0% Buffer B |
| 5-35 min: | 0-5% Buffer B |
| 35-40 min: | 50-100% Buffer B |

The elution patterns of the protein (OD=280 nm) and the activity on Resource Q column chromatography are shown in FIG. 1. When FAO activity was monitored using FV as a substrate, two fractions (Q1 and Q2) were found to have activity. Measurement of activity was performed in a similar manner to that described in Example 1 (3). FAOs contained in these fractions are herein referred to as "FAO-Q1" and "FAO-Q2".

TABLE 1

Change of Activity according to Purification Steps

| Step | | total unit(U) | specific activity(U/mg) | yield(%) |
|---|---|---|---|---|
| Cell-free extract | | 0.5 | 0.019 | 100 |
| After fractionation dialysis with 30-80% ammonium sulfate | | 0.3 | 0.0199 | 60 |
| Resource Q | Q1 | 0.22 | 0.3 | 44 |
| | Q2 | 0.03 | 0.067 | 6 |

(2) Comparison of Substrate Specificity of FAO-Q1 and FAO-Q2

The substrate specificity of the enzymes (FAO-Q1, FAO-Q2) contained in 2 fractions separated in (1), 3) above was determined. The FAO activity was measured using the respective two fractions as an enzyme solution according to the method described in Example 1(3). As a substrate, FV, FVH, FVHL, FVL, FVLS and FZL were used. The results are shown in Table 2.

TABLE 2

Substrate Specificity of FAO-Q1 and FAO-Q2

| | Relative activity (%) | |
|---|---|---|
| | FAO-Q1 | FAO-Q2 |
| FV | 100 | 100 |
| FVH | n.d. | 2.4 |
| FVHL | n.d. | 0.6 |
| FVL | 1.1 | 0.6 |
| FVLS | n.d. | 3.3 |
| FZL | 108 | n.d. |

FV: fructosyl valine; FVH: fructosyl valine-histidine; FVHL: fructosyl valine-histidine-leucine; FVL: fructosyl valine-leucine; FVLS: fructosyl valine-leucine-serine; FZL: fructosyl N-α-lysine n.d.: not detected It is clear from Table 2 that FAO-Q1 is almost equally active on both of FV and FZL, and on FVL as well, and that FAO-Q2 is active on FV but inactive on FZL, and is active on FVH and FVHL wherein N-terminal valine is glycated.

(3) Measurement of Km values

Km value (Michaelis constant) of FAO-Q1 or FAO-Q2 for FV or FZL were determined by measuring the activity according to the method described in Example 1(3) using as a substrate FV or FZL. The results are shown in Table 3.

TABLE 3

Km Values of FAO-Q1 and FAO-Q2 for FV or FZL

| | FAO-Q1 | FAO-Q2 |
|---|---|---|
| FV | 0.62 | 0.64 |
| FZL | 0.56 | n.d. | n.d. not detected

FAO-Q1 and FAO-Q2 were comparable in Km value for FV. On the other hand, FAO-Q1 had smaller Km value for FZL than that for FV, indicating that said enzyme have a greater affinity for FV.

1) SDS Electrophoresis

The molecular weight was determined by SDS electrophoresis using a gradient gel (gel concentration: 10-15 w/v %). The molecular weight of FAO-Q1 was about 39 kDa and that of FAO-Q2 was about 49 kDa, when measured using molecular weight markers (phosphorylase b: 97 kDa; bovine serum albumin: 68 kDa, ovalbumin: 45 kDa, carbonic anhydrase: 32 kDa, trypsin inhibitor: 20.1 kDa, and α-lactoalbumin: 14.4 kDa; Amersham Biosciences K.K.) as standard proteins of known molecular weight.

2) Gel Filtration

The molecular weight was determined by gel filtration in a conventional manner using Superdex 200 (column size: 1×30 cm; Amersham Biosciences K.K.). The molecular weight of the enzymes of the present invention was calculated using a standard curve obtained from molecular weight markers (aldolase: 150 kDa, bovine serum albumin: 68 kDa, ovalbumin: 45 kDa, chymotrypsinogen A: 25 kDa, and cytochrome C: 12.5 kDa; Roche Diagnostics K.K.). The results are shown in FIG. 2. It was revealed that the molecular weight of FAO-Q1 is about 39.4 kDa and that of FAO-Q2 about 58 kDa.

(5) Analysis of Partial Amino Acid Sequence

In order to determine the N-terminal amino acid sequence, the purified FAO-Q2 enzyme was dialyzed against distilled water and 40 ng of the same was used as the sample for N-terminal amino acid sequencing. N-terminal 10 residues were analyzed using Protein Sequencer model 476A (Applied Biosystems, USA). The N-terminal sequence of FAO-Q2 was revealed to be the same as the amino acid sequence shown in SEQ ID NO: 2. On the other hand, it was impossible to determine the sequence of FAO-Q1 in this way because the N-terminus was blocked.

EXAMPLE 3

Cloning of FAO cDNA

Genomic DNA of GL2-1 was prepared. FAO cDNA was then obtained by PCR using as a template the genomic DNA.

(1) Preparation of Genomic DNA of GL2-1 Strain

The genomic DNA was prepared from GL2-1 strain according to a process comprising the following steps.

1. GL2-1 strain is liquid-cultured in 15 ml of DP medium (1% Dextone, 1% Peptone and 0.5% NaCl, pH 7.4) at 30° C. for 2 to 3 days.

2. Fungal cells (wet weight, 0.3 g) are collected by filtration through glass filter (3GL).

3. The resultant fungal cells are homogenized in a mortar containing liquid nitrogen with a pestle, further ground in a motor or the like, and then collected in a Corning tube.

4. After adding 2 ml of ice-cold TE buffer (10 mM Tris-HCl (pH8.0), 1 mM EDTA), the mixture is vortexed lightly.

5. After adding 2 ml of a solution of 50 mM EDTA and 0.5% SDS, the mixture is stirred by rotating several times and incubated at 37° C. for 30 minutes.

6. The mixture is centrifuged (3,000 rpm, 10 minutes).

7. The supernatant is treated with phenol-chloroform (3 times) wherein stirring is conducted by rotation.

8. After adding 2.5 volumes of ethanol, the mixture is stirred by rotating several times. At this stage, filamentous DNA appears.

9. The mixture is briefly centrifuged (3,000 rpm, 5 minutes) to sediment filamentous DNA. When DNA does not become filamentous, the mixture is centrifuged according to the normal ethanol precipitation.

10. The precipitates are dissolved in 400 µl of TE buffer (10 mM Tris-HCl (pH8.0), 1 mM EDTA; hereinafter, "TE buffer"

has the same meaning), and transferred into an Eppendorf tube. After adding 5 µl of RNase (10 mg/ml), it is incubated at 37° C. for 30 minutes.

11. After treating two times with phenol-chloroform, 2.5 volume of ethanol is added to the tube, which is followed by stirring thoroughly by rotation.

12. The filamentous DNA is transferred to a new tube with toothpick (excess ethanol is removed).

13. DNA is dissolved in 50-100 µl of TE buffer (pipetting gently but not vortex).

14. DNA is quantitatively determined. DNA (1 µg) was electrophoresed on agarose gel to confirm a band(s).

(2) Preparation of cDNA by PCR

1) Preparation of Partial Sequence (About 200 bp Fragment)

A search for a region with high homology was carried out using an already-known total amino acid sequence of an FAOD from filamentous fungus. The following primers were designed on the basis of resulting information.

Primers:

```
                                               SEQ ID NO:7
Forward primer:    5'-GGBTTYTTCWTSGARCCNRAYGA-3'

SEQ ID NO:8
Reverse primer:    5'-GTRCVGYRYMCCAGCAVAT-3'
```

PCR was performed using the above genome DNA as a template in a reaction solution of standard composition using Taq polymerase (TaKaRa Ex Taq, TAKARA BIO INC.).

PCR Condition:

| | |
|---|---|
| Primer (SEQ ID NO: 7) | 0.2 µM |
| Primer (SEQ ID NO: 8) | 0.2 µM |
| 10 ExTaq PCR buffer (TAKARA BIO INC.) | 10 µl |
| Magnesium Chloride | 2.5 mM |
| Taq Polymerase (TAKARA BIO INC.) | 2.5 U |

D.D.W. (double deionized water) was added to make the total volume 100 µl.

One cycle of 94° C. for 1 minute; 35 cycles of (94° C. for 1 minute, 50° C. for 1 minute and 72° C. for 1 minute); and 1 cycle of 72° C. for 3 minutes.

After completion of PCR, 10 µl of reaction solution was electrophoresed on agarose gel and a band assumed to be the objective fragment was observed at 200 bp. The band was excised, treated with TOPO TA Cloning Kit (Invitrogen) according to the instructions attached to the kit, and transformed into *E. coli* JM 109. Twenty transformants were selected arbitrarily, and subjected to extraction of plasmid. Each plasmid was treated with restriction enzyme, and a plasmid(s) containing a DNA of appropriate size was selected and sequenced. The sequencing was performed using BigDye Terminator Cycle Sequence Kit and, as a sequencer, ABI PRISM3 100 Genetic Analyzer.

As a result, two base sequences (polynucleotides) possibly corresponding to two isozymes (FAO-Q1 and FAO-Q2) were obtained. In the putative amino acid sequence deduced from the thus determined base sequence, the amino acid sequence of purified enzyme was confirmed. It was revealed that the DNA fragments amplified by PCR above contain a portion of genes each encoding FAO-Q1 and FAO-Q2, respectively.

2) Preparation of Upstream or Downstream Partial Sequences and Total DNA

DNA sequences of upstream and downstream regions were determined from the two 200 bp fragments obtained in 1) above using TaKaRa LA PCR in vitro Cloning Kit. The resultant base sequences of FAO-Q1 and FAO-Q2 are shown in SEQ ID NO: 3 and SEQ ID NO: 5, respectively. The deduced amino acid sequences encoded thereby are shown in SEQ ID NO: 4 and SEQ ID NO: 6, respectively.

INDUSTRIAL APPLICABILITY

The present invention provides novel FAOs, which are expected to contribute to development of analysis of amadori compounds. In particular, using, among the present FAOs, an enzyme having activity on glycated peptide as well as glycated amino acid makes it possible to measure a glycated protein more accurately even if fragmentation of glycated protein is not perfect. As a result, HbA1c which is important for control of glucose level in blood in diabetic patients can be determined accurately, and thereby contributing to the treatment of diabetes and the prevention of complications in diabetic patients. Furthermore, the DNA encoding the novel fructosylamine oxidase of the present invention is expected to enable the efficient large-scale production of the enzyme by means of gene recombinant techniques, and thereby accelerating the development of analysis of amadori compounds.

The invention claimed is:

1. An isolated fructosylamine oxidase enzyme from *Fusarium proliferatum*, which has the following physico-chemical characteristics:
   (1) It is equally or more active on fructosyl valine as compared to fructosyl lysine;
   (2) The optimum pH for its enzyme reaction is 7.5;
   (3) The optimum temperature for stability of the enzyme is about 30-40° C.; and
   (4) The molecular weight of the enzyme is about 39 kDa when estimated by SDS-PAGE, and is about 39.4 kDa when measured by gel filtration, wherein said fructosylamine oxidase comprises the amino acid sequence shown in SEQ ID NO: 4.

2. An isolated fructosylamine oxidase enzyme from *Fusarium proliferatum*, which has the following physico-chemical characteristics:
   (1) It is active on fructosyl valine;
   (2) The optimum pH for its enzyme reaction is 7;
   (3) The optimum temperature for stability of the enzyme is about 30-40° C.; and
   (4) The molecular weight of the enzyme is about 49 kDa when estimated by SDS-PAGE, and is about 58 kDa when measured by gel filtration, wherein said fructosylamine oxidase comprises the amino acid sequence shown in SEQ ID NO: 6.

* * * * *

UNITED STATES PATENT AND TRADEMARK OFFICE
CERTIFICATE OF CORRECTION

PATENT NO.         : 7,407,783 B2
APPLICATION NO.    : 10/528992
DATED              : August 5, 2008
INVENTOR(S)        : Nobuyuki Yoshida et al.

It is certified that error appears in the above-identified patent and that said Letters Patent is hereby corrected as shown below:

<u>On the Title Page</u>

Item (73) Assignee: Please add the Assignee as follows:

--Assignee: ARKRAY, INC., Kyoto-shi (JP)--.

Signed and Sealed this

Seventh Day of April, 2009

JOHN DOLL
*Acting Director of the United States Patent and Trademark Office*

SEQUENCE LISTING

```
<160> NUMBER OF SEQ ID NOS: 8

<210> SEQ ID NO 1
<211> LENGTH: 460
<212> TYPE: DNA
<213> ORGANISM: Fusarium proliferatum

<400> SEQUENCE: 1
aactcccaaa ccctgtgaa cataccaatt gttgcctcgg cggatcagcc cgctcccggt     60
aaaacgggac ggcccgccag aggacccta aactctgttt ctatatgtaa cttctgagta    120 aaccataaa taaatcaaaa cttttcaacaa cggatctctt ggttctggca tcgatgaaga    180
acgcagcaaa atgcgataag taatgtgaat tgcagaattc agtgaatcat cgaatctttg    240
aacgcacatt gcgcccgcca gtattctggc gggcatgcct gttcgagcgt catttcaacc    300
ctcaagcccc cgggtttggt gttggggatc ggcgagccct tgcggcaagc cggccccgaa    360
atctagtggc ggtctcgctg cagcttccat tgcgtagtag taaaaccctc gcaactggta    420
cgcggcgcgg ccaagccgtt aaaccccaa cttctgaatg                           460

<210> SEQ ID NO 2
<211> LENGTH: 10
<212> TYPE: PRT
<213> ORGANISM: Fusarium proliferatum

<400> SEQUENCE: 2

Ala Arg Thr Val Ala Pro Leu Asn Lys Asp
  1               5                  10

<210> SEQ ID NO 3
<211> LENGTH: 1422
<212> TYPE: DNA
<213> ORGANISM: Fusarium proliferatum
<220> FEATURE:
<221> NAME/KEY: CDS
<222> LOCATION: (1)..(1419)

<400> SEQUENCE: 3 atg gcc ggt cct ccc tct tcc atc ctt atc gtt ggc tct gga gtc ttc     48
Met Ala Gly Pro Pro Ser Ser Ile Leu Ile Val Gly Ser Gly Val Phe
  1               5                  10                  15 ggg ctc ggt acc gcc tgg gct ttg gcc aaa cga tca cac ttt tcc aac     96
Gly Leu Gly Thr Ala Trp Ala Leu Ala Lys Arg Ser His Phe Ser Asn
                 20                  25                  30 acc tcg att act gtc gtc gac gac tgc gca gga cag ttt cct cca gaa    144
Thr Ser Ile Thr Val Val Asp Asp Cys Ala Gly Gln Phe Pro Pro Glu
             35                  40                  45
```

```
gat gct gcc agt gta gac tcg tct cgc att gta cga gcc gac tac tcg     192
Asp Ala Ala Ser Val Asp Ser Ser Arg Ile Val Arg Ala Asp Tyr Ser
     50              55                  60 gac cct tac tat gcc gcg ctt gcc gcc gag gcg cag aag gaa tgg cga     240
Asp Pro Tyr Tyr Ala Ala Leu Ala Ala Glu Ala Gln Lys Glu Trp Arg
 65          70                  75                      80 aag cag ggt gat cat gag gtc ggt ggg cag gga cga tat tcc gag tcg     288
Lys Gln Gly Asp His Glu Val Gly Gly Gln Gly Arg Tyr Ser Glu Ser
                 85                  90                  95 ggc ttt gtt ctc tgc gcg agc gag act cct gaa gac ttc aag ctc aag     336
Gly Phe Val Leu Cys Ala Ser Glu Thr Pro Glu Asp Phe Lys Leu Lys
             100                 105                 110 aag tct ggc atg gac tac acc aag gag agc gcc aaa aac gtc gag ttg     384
Lys Ser Gly Met Asp Tyr Thr Lys Glu Ser Ala Lys Asn Val Glu Leu
         115                 120                 125 att gct aag gag act ggt ctg ccc gtg gat aag atc cag aag ctg gag     432
Ile Ala Lys Glu Thr Gly Leu Pro Val Asp Lys Ile Gln Lys Leu Glu
 130                 135                 140 agt acc aag gct ctc caa gag ttc ctt ggc aca gac ggt tat ccc gga     480
Ser Thr Lys Ala Leu Gln Glu Phe Leu Gly Thr Asp Gly Tyr Pro Gly
145                 150                 155                 160 gac tgg ggc tac ctc aat ggc aac tct ggc tgg gct gat gcc ggg gag     528
Asp Trp Gly Tyr Leu Asn Gly Asn Ser Gly Trp Ala Asp Ala Gly Glu
                 165                 170                 175 ggt atg aag tgg ctc tat aag cag gcc cag gcc aca gga cgt att cat     576
Gly Met Lys Trp Leu Tyr Lys Gln Ala Gln Ala Thr Gly Arg Ile His
             180                 185                 190 ttt gtc aac ggc aag gtg aca gag ctc gta aca gag ggt gac cga gtc     624
Phe Val Asn Gly Lys Val Thr Glu Leu Val Thr Glu Gly Asp Arg Val
         195                 200                 205 att ggt gcg aaa ttg agc gat tca aag att ctc aag gcc gat gtg gtt     672
Ile Gly Ala Lys Leu Ser Asp Ser Lys Ile Leu Lys Ala Asp Val Val
 210                 215                 220 atg gta gct gct ggt gct tgg tcc ggc tca ctc gtt gac ctt cga gga     720
Met Val Ala Ala Gly Ala Trp Ser Gly Ser Leu Val Asp Leu Arg Gly
225                 230                 235                 240 aga aca gag gct act ggc cat gct gtc gcg tat atg gac atc aca ccg     768
Arg Thr Glu Ala Thr Gly His Ala Val Ala Tyr Met Asp Ile Thr Pro
                 245                 250                 255 gaa gag cag aag cga ctc gac aac ttc cct gtg gtg ttg aat ctc agc     816
Glu Glu Gln Lys Arg Leu Asp Asn Phe Pro Val Val Leu Asn Leu Ser
             260                 265                 270 acc ggt ctc ttc ctc att cct cct cga aat aac gtc ctc aag gcc gcc     864
Thr Gly Leu Phe Leu Ile Pro Pro Arg Asn Asn Val Leu Lys Ala Ala
         275                 280                 285 cga cac aca ttc ggg tac att aac ccg gtc aag att aac aac gct ctt     912
Arg His Thr Phe Gly Tyr Ile Asn Pro Val Lys Ile Asn Asn Ala Leu
 290                 295                 300 cct cct tcg ccc aac gat aag cgg gaa cca ttc atc gca tct caa ccc     960
Pro Pro Ser Pro Asn Asp Lys Arg Glu Pro Phe Ile Ala Ser Gln Pro
305                 310                 315                 320 tac acc tct cgc aac gat tcc tca aat cct tta acc gtc gag gct gac    1008
Tyr Thr Ser Arg Asn Asp Ser Ser Asn Pro Leu Thr Val Glu Ala Asp
                 325                 330                 335 aaa gat ctg cgc cgc gca ctc acg gat ctg tgt cct ata cgt ggc cta    1056
Lys Asp Leu Arg Arg Ala Leu Thr Asp Leu Cys Pro Ile Arg Gly Leu
             340                 345                 350 gaa acc agg cca tgg aag gag gct cga atc tgc tgg tat tcc gat aca    1104
Glu Thr Arg Pro Trp Lys Glu Ala Arg Ile Cys Trp Tyr Ser Asp Thr
         355                 360                 365
```

```
cga gat ggc gag tgg ctc att gac tac cac ccg ggc tgg aag gga ctc     1152
Arg Asp Gly Glu Trp Leu Ile Asp Tyr His Pro Gly Trp Lys Gly Leu
    370                 375                 380 ttt gtt gca aca ggt gac agt gga cac gga ttc aag ttc cta ccc aac     1200
Phe Val Ala Thr Gly Asp Ser Gly His Gly Phe Lys Phe Leu Pro Asn
385                 390                 395                 400 ttg ggt gag aaa atc gtg gat gtt atg caa ggc cag ggt ggc aag ctt     1248
Leu Gly Glu Lys Ile Val Asp Val Met Gln Gly Gln Gly Gly Lys Leu
                405                 410                 415 ggc gag aag tgg cga tgg aaa gag atc cag aat gat gga gtc gga aga     1296
Gly Glu Lys Trp Arg Trp Lys Glu Ile Gln Asn Asp Gly Val Gly Arg
            420                 425                 430 gag acg aac gga gtg tac act ggt tta gtg acg gaa gat ggt agc aga     1344
Glu Thr Asn Gly Val Tyr Thr Gly Leu Val Thr Glu Asp Gly Ser Arg
        435                 440                 445 ggt gga cgg ccc ttg gtg ctc tgt gat gag ctc gag aag ggc agg gcg     1392
Gly Gly Arg Pro Leu Val Leu Cys Asp Glu Leu Glu Lys Gly Arg Ala
    450                 455                 460 ctt att ggg aac acc aag gcc aag cta tga                             1422
Leu Ile Gly Asn Thr Lys Ala Lys Leu
465                 470
```

<210> SEQ ID NO 4
<211> LENGTH: 473
<212> TYPE: PRT
<213> ORGANISM: Fusarium proliferatum

<400> SEQUENCE: 4

```
Met Ala Gly Pro Pro Ser Ser Ile Leu Ile Val Gly Ser Gly Val Phe
1               5                   10                  15

Gly Leu Gly Thr Ala Trp Ala Leu Ala Lys Arg Ser His Phe Ser Asn
            20                  25                  30

Thr Ser Ile Thr Val Val Asp Asp Cys Ala Gly Gln Phe Pro Pro Glu
        35                  40                  45

Asp Ala Ala Ser Val Asp Ser Ser Arg Ile Val Arg Ala Asp Tyr Ser
    50                  55                  60

Asp Pro Tyr Tyr Ala Ala Leu Ala Ala Glu Ala Gln Lys Glu Trp Arg
65                  70                  75                  80

Lys Gln Gly Asp His Glu Val Gly Gly Gln Gly Arg Tyr Ser Glu Ser
                85                  90                  95

Gly Phe Val Leu Cys Ala Ser Glu Thr Pro Glu Asp Phe Lys Leu Lys
            100                 105                 110

Lys Ser Gly Met Asp Tyr Thr Lys Glu Ser Ala Lys Asn Val Glu Leu
        115                 120                 125

Ile Ala Lys Glu Thr Gly Leu Pro Val Asp Lys Ile Gln Lys Leu Glu
    130                 135                 140

Ser Thr Lys Ala Leu Gln Glu Phe Leu Gly Thr Asp Gly Tyr Pro Gly
145                 150                 155                 160

Asp Trp Gly Tyr Leu Asn Gly Asn Ser Gly Trp Ala Asp Ala Gly Glu
                165                 170                 175

Gly Met Lys Trp Leu Tyr Lys Gln Ala Gln Ala Thr Gly Arg Ile His
            180                 185                 190

Phe Val Asn Gly Lys Val Thr Glu Leu Val Thr Glu Gly Asp Arg Val
        195                 200                 205

Ile Gly Ala Lys Leu Ser Asp Ser Lys Ile Leu Lys Ala Asp Val Val
    210                 215                 220
```

```
Met Val Ala Ala Gly Ala Trp Ser Gly Ser Leu Val Asp Leu Arg Gly
225                 230                 235                 240

Arg Thr Glu Ala Thr Gly His Ala Val Ala Tyr Met Asp Ile Thr Pro
            245                 250                 255

Glu Glu Gln Lys Arg Leu Asp Asn Phe Pro Val Val Leu Asn Leu Ser
                260                 265                 270

Thr Gly Leu Phe Leu Ile Pro Pro Arg Asn Asn Val Leu Lys Ala Ala
            275                 280                 285

Arg His Thr Phe Gly Tyr Ile Asn Pro Val Lys Ile Asn Asn Ala Leu
        290                 295                 300

Pro Pro Ser Pro Asn Asp Lys Arg Glu Pro Phe Ile Ala Ser Gln Pro
305                 310                 315                 320

Tyr Thr Ser Arg Asn Asp Ser Ser Asn Pro Leu Thr Val Glu Ala Asp
                325                 330                 335

Lys Asp Leu Arg Arg Ala Leu Thr Asp Leu Cys Pro Ile Arg Gly Leu
            340                 345                 350

Glu Thr Arg Pro Trp Lys Glu Ala Arg Ile Cys Trp Tyr Ser Asp Thr
        355                 360                 365

Arg Asp Gly Glu Trp Leu Ile Asp Tyr His Pro Gly Trp Lys Gly Leu
370                 375                 380

Phe Val Ala Thr Gly Asp Ser Gly His Gly Phe Lys Phe Leu Pro Asn
385                 390                 395                 400

Leu Gly Glu Lys Ile Val Asp Val Met Gln Gly Gln Gly Gly Lys Leu
                405                 410                 415

Gly Glu Lys Trp Arg Trp Lys Glu Ile Gln Asn Asp Gly Val Gly Arg
            420                 425                 430

Glu Thr Asn Gly Val Tyr Thr Gly Leu Val Thr Glu Asp Gly Ser Arg
        435                 440                 445

Gly Gly Arg Pro Leu Val Leu Cys Asp Glu Leu Glu Lys Gly Arg Ala
    450                 455                 460

Leu Ile Gly Asn Thr Lys Ala Lys Leu
465                 470

<210> SEQ ID NO 5
<211> LENGTH: 1335
<212> TYPE: DNA
<213> ORGANISM: Fusarium proliferatum
<220> FEATURE:
<221> NAME/KEY: CDS
<222> LOCATION: (1)..(1332)

<400> SEQUENCE: 5 atg gcc cgt act gtt gcc ccg ctc aat aag gac tca ggg att ctc atc      48
Met Ala Arg Thr Val Ala Pro Leu Asn Lys Asp Ser Gly Ile Leu Ile
1               5                   10                  15 gtt ggt ggc gga act tgg gga tgc tca act gcc ctc cat ctc gcc cgt      96
Val Gly Gly Gly Thr Trp Gly Cys Ser Thr Ala Leu His Leu Ala Arg
            20                  25                  30 cgg ggt tac acc aac gtc act gtt ctc gat gtc aat cgc atc ccg tca     144
Arg Gly Tyr Thr Asn Val Thr Val Leu Asp Val Asn Arg Ile Pro Ser
        35                  40                  45 ccg ata tca gcc ggg cat gat gta aac aaa ctt tct aac aga cta ggc     192
Pro Ile Ser Ala Gly His Asp Val Asn Lys Leu Ser Asn Arg Leu Gly
    50                  55                  60 act tct gat agt aaa ggc gat gac gaa gac tca atc tgg aaa gct ctt     240
Thr Ser Asp Ser Lys Gly Asp Asp Glu Asp Ser Ile Trp Lys Ala Leu
65                  70                  75                  80
```

```
acg tac gcc gca gct caa gga tgg ctc cat gat ccc atc ttc caa cct    288
Thr Tyr Ala Ala Ala Gln Gly Trp Leu His Asp Pro Ile Phe Gln Pro
                85                  90                  95 ttc tgc cac aat aca gga gct gtc atg gct ggc tca aca cca aaa tct    336
Phe Cys His Asn Thr Gly Ala Val Met Ala Gly Ser Thr Pro Lys Ser
            100                 105                 110 atc aag cag ctg gta gaa gat gag atc ggt gac gac atc gac cag tat    384
Ile Lys Gln Leu Val Glu Asp Glu Ile Gly Asp Asp Ile Asp Gln Tyr
        115                 120                 125 aca cct ctc aac aca gca gaa gat ttc aga agg act atg ccg gag cgt    432
Thr Pro Leu Asn Thr Ala Glu Asp Phe Arg Arg Thr Met Pro Glu Arg
    130                 135                 140 att ctg aca ggt gat ttt cta ggc tgg aag ggc ttt tac aag ccc aga    480
Ile Leu Thr Gly Asp Phe Leu Gly Trp Lys Gly Phe Tyr Lys Pro Arg
145                 150                 155                 160 ggt tca ggt tgg gtt cat gcc aga aag gct atg aaa gct gct ttt gaa    528
Gly Ser Gly Trp Val His Ala Arg Lys Ala Met Lys Ala Ala Phe Glu
                165                 170                 175 gag agc cag aga ctt ggt gtc aag ttc atc act ggc tct ccc gaa ggc    576
Glu Ser Gln Arg Leu Gly Val Lys Phe Ile Thr Gly Ser Pro Glu Gly
            180                 185                 190 aag gtc gag agt ctg gtc ttt gaa gct ggt gat gtc aaa ggt gca aaa    624
Lys Val Glu Ser Leu Val Phe Glu Ala Gly Asp Val Lys Gly Ala Lys
        195                 200                 205 aca gca gat gga aag gaa cac aga gcg gat cga aca att ctc tcc gct    672
Thr Ala Asp Gly Lys Glu His Arg Ala Asp Arg Thr Ile Leu Ser Ala
    210                 215                 220 ggt gcc tca gca gag ttc tcc ctc gat ttt gag aac cag atc cgt cct    720
Gly Ala Ser Ala Glu Phe Ser Leu Asp Phe Glu Asn Gln Ile Arg Pro
225                 230                 235                 240 acg gca tgg act ctg ggc cat atc cag atg aca gca gag gaa aca aag    768
Thr Ala Trp Thr Leu Gly His Ile Gln Met Thr Ala Glu Glu Thr Lys
                245                 250                 255 ctg tac aag gaa ctt ccc ccc ctt ttc aat atc aac cag ggc ttc ttc    816
Leu Tyr Lys Glu Leu Pro Pro Leu Phe Asn Ile Asn Gln Gly Phe Phe
            260                 265                 270 atg gaa ccc gat gag gac ttg cat caa ctc aag atg tgc gat gaa cat    864
Met Glu Pro Asp Glu Asp Leu His Gln Leu Lys Met Cys Asp Glu His
        275                 280                 285 ccc gga tac tgc aat tgg gtt gac aaa cct ggt tcc aaa tac ccc cag    912
Pro Gly Tyr Cys Asn Trp Val Asp Lys Pro Gly Ser Lys Tyr Pro Gln
    290                 295                 300 tcc atc ccc ttc gca aag tat caa gtg cca att gag gct gaa cga cgc    960
Ser Ile Pro Phe Ala Lys Tyr Gln Val Pro Ile Glu Ala Glu Arg Arg
305                 310                 315                 320 atg aag caa ttt ctg aaa gac atc atg cct cag ctc gca gat cgg cca   1008
Met Lys Gln Phe Leu Lys Asp Ile Met Pro Gln Leu Ala Asp Arg Pro
                325                 330                 335 ctt gtt cat gct cga atc tgc tgg tgc gcc gat aca cag gat aga atg   1056
Leu Val His Ala Arg Ile Cys Trp Cys Ala Asp Thr Gln Asp Arg Met
            340                 345                 350 ttt ctg atc acg tat cac cct cga cac cca tcg ctt gtc att gct tcc   1104
Phe Leu Ile Thr Tyr His Pro Arg His Pro Ser Leu Val Ile Ala Ser
        355                 360                 365 ggg gat tgt ggc aca gga tac aag cat atc act tcc att gga aag ttc   1152
Gly Asp Cys Gly Thr Gly Tyr Lys His Ile Thr Ser Ile Gly Lys Phe
    370                 375                 380 atc tct gat tgt atg gag ggc aca ttg gag gaa agg ttt gct aag ttc   1200
Ile Ser Asp Cys Met Glu Gly Thr Leu Glu Glu Arg Phe Ala Lys Phe
385                 390                 395                 400
```

-continued

```
tgg aga tgg cga cca gag aag ttt acg gag ttc tgg ggt aaa gat ccc     1248
Trp Arg Trp Arg Pro Glu Lys Phe Thr Glu Phe Trp Gly Lys Asp Pro
            405                 410                 415 ctg gat cgg ttt gga gct gac gat aag atc atg gat ttg ccc aag agt     1296
Leu Asp Arg Phe Gly Ala Asp Asp Lys Ile Met Asp Leu Pro Lys Ser
            420                 425                 430 gat gca gag gga tgg aca gac ata cag aat gat aaa taa                 1335
Asp Ala Glu Gly Trp Thr Asp Ile Gln Asn Asp Lys
            435                 440
```

<210> SEQ ID NO 6
<211> LENGTH: 444
<212> TYPE: PRT
<213> ORGANISM: Fusarium proliferatum

<400> SEQUENCE: 6

```
Met Ala Arg Thr Val Ala Pro Leu Asn Lys Asp Ser Gly Ile Leu Ile
1               5                   10                  15

Val Gly Gly Gly Thr Trp Gly Cys Ser Thr Ala Leu His Leu Ala Arg
                20                  25                  30

Arg Gly Tyr Thr Asn Val Thr Val Leu Asp Val Asn Arg Ile Pro Ser
            35                  40                  45

Pro Ile Ser Ala Gly His Asp Val Asn Lys Leu Ser Asn Arg Leu Gly
        50                  55                  60

Thr Ser Asp Ser Lys Gly Asp Asp Glu Asp Ser Ile Trp Lys Ala Leu
65                  70                  75                  80

Thr Tyr Ala Ala Ala Gln Gly Trp Leu His Asp Pro Ile Phe Gln Pro
                85                  90                  95

Phe Cys His Asn Thr Gly Ala Val Met Ala Gly Ser Thr Pro Lys Ser
            100                 105                 110

Ile Lys Gln Leu Val Glu Asp Glu Ile Gly Asp Asp Ile Asp Gln Tyr
        115                 120                 125

Thr Pro Leu Asn Thr Ala Glu Asp Phe Arg Arg Thr Met Pro Glu Arg
130                 135                 140

Ile Leu Thr Gly Asp Phe Leu Gly Trp Lys Gly Phe Tyr Lys Pro Arg
145                 150                 155                 160

Gly Ser Gly Trp Val His Ala Arg Lys Ala Met Lys Ala Ala Phe Glu
                165                 170                 175

Glu Ser Gln Arg Leu Gly Val Lys Phe Ile Thr Gly Ser Pro Glu Gly
            180                 185                 190

Lys Val Glu Ser Leu Val Phe Glu Ala Gly Asp Val Lys Gly Ala Lys
        195                 200                 205

Thr Ala Asp Gly Lys Glu His Arg Ala Asp Arg Thr Ile Leu Ser Ala
210                 215                 220

Gly Ala Ser Ala Glu Phe Ser Leu Asp Phe Glu Asn Gln Ile Arg Pro
225                 230                 235                 240

Thr Ala Trp Thr Leu Gly His Ile Gln Met Thr Ala Glu Glu Thr Lys
                245                 250                 255

Leu Tyr Lys Glu Leu Pro Pro Leu Phe Asn Ile Asn Gln Gly Phe Phe
            260                 265                 270

Met Glu Pro Asp Glu Asp Leu His Gln Leu Lys Met Cys Asp Glu His
        275                 280                 285

Pro Gly Tyr Cys Asn Trp Val Asp Lys Pro Gly Ser Lys Tyr Pro Gln
        290                 295                 300

Ser Ile Pro Phe Ala Lys Tyr Gln Val Pro Ile Glu Ala Glu Arg Arg
305                 310                 315                 320
```

-continued

```
Met Lys Gln Phe Leu Lys Asp Ile Met Pro Gln Leu Ala Asp Arg Pro
                325                 330                 335

Leu Val His Ala Arg Ile Cys Trp Cys Ala Asp Thr Gln Asp Arg Met
                340                 345                 350

Phe Leu Ile Thr Tyr His Pro Arg His Pro Ser Leu Val Ile Ala Ser
                355                 360                 365

Gly Asp Cys Gly Thr Gly Tyr Lys His Ile Thr Ser Ile Gly Lys Phe
            370                 375                 380

Ile Ser Asp Cys Met Glu Gly Thr Leu Glu Glu Arg Phe Ala Lys Phe
385                 390                 395                 400

Trp Arg Trp Arg Pro Glu Lys Phe Thr Glu Phe Trp Gly Lys Asp Pro
                405                 410                 415

Leu Asp Arg Phe Gly Ala Asp Asp Lys Ile Met Asp Leu Pro Lys Ser
                420                 425                 430

Asp Ala Glu Gly Trp Thr Asp Ile Gln Asn Asp Lys
            435                 440
```

<210> SEQ ID NO 7
<211> LENGTH: 23
<212> TYPE: PRT
<213> ORGANISM: Artificial Sequence
<220> FEATURE:
<223> OTHER INFORMATION: A peptide designed on the basis of the
      peptide produced by Fusarium proliferatum

<400> SEQUENCE: 7

```
Gly Gly Asx Thr Thr Tyr Thr Thr Cys Trp Ser Gly Ala Arg Cys
1               5                   10                  15

Cys Asn Arg Ala Tyr Gly Ala
            20
```

<210> SEQ ID NO 8
<211> LENGTH: 19
<212> TYPE: PRT
<213> ORGANISM: Artificial Sequence
<220> FEATURE:
<223> OTHER INFORMATION: A peptide designed on the basis of the
      peptide produced by Fusarium proliferatum

<400> SEQUENCE: 8

```
Gly Thr Arg Cys Val Gly Tyr Arg Tyr Met Cys Cys Ala Gly Cys Ala
1               5                   10                  15

Val Ala Thr
```